United States Patent
Terry, Jr. et al.

(10) Patent No.: US 6,473,644 B1
(45) Date of Patent: Oct. 29, 2002

(54) METHOD TO ENHANCE CARDIAC CAPILLARY GROWTH IN HEART FAILURE PATIENTS

(75) Inventors: Reese S. Terry, Jr.; Burke Barrett, both of Houston; Alan Adkins, Angleton, all of TX (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 09/417,080

(22) Filed: Oct. 13, 1999

(51) Int. Cl.[7] ................................................. A61N 1/36
(52) U.S. Cl. ................................................. 607/2; 607/9
(58) Field of Search .................................. 607/2, 14, 9

(56) References Cited

U.S. PATENT DOCUMENTS

| | | | |
|---|---|---|---|
| 5,330,507 A | * 7/1994 | Schwartz | 607/14 |
| 5,651,378 A | * 7/1997 | Matheny et al. | 607/9 |
| 5,690,681 A | * 11/1997 | Geddes et al. | 607/2 |
| 5,700,282 A | * 12/1997 | Zabara | 607/9 |
| 5,913,876 A | * 6/1999 | Taylor et al. | 607/2 |
| 6,141,586 A | * 10/2000 | Mower | 607/9 |

* cited by examiner

Primary Examiner—Carl Layno
(74) Attorney, Agent, or Firm—Blank Rome Comisky & McCauley LLP

(57) ABSTRACT

A method is disclosed for treating patients suffering from heart failure to increase cardiac output. The patient's vagus nerve is electrically stimulated or modulated with a sequence of substantially equally spaced pulses by an implanted neurostimulator, and the frequency of the stimulating pulses is adjusted until the patient's heart rate reaches a target rate within a relatively stable target rate range below the low end of the patient's customary resting heart rate. The frequency of the stimulating pulses is maintained at the frequency which ultimately produced the relatively stable target rate range so as not to deviate markedly from the target rate, at least so long as the patient remains at rest. An activity sensor associated with the implanted neurostimulator detects physical activity of the patient and adjusts the frequency of the stimulating pulses accordingly, to elevate the heart rate during periods of physical activity by the patient. When the patient ceases the activity, the vagal stimulation reverts along a prescribed fall-back path to a frequency that will reproduce the target heart rate.

41 Claims, 2 Drawing Sheets

METHOD TO ENHANCE CARDIAC CAPILLARY GROWTH IN HEART FAILURE PATIENTS

BACKGROUND OF THE INVENTION

The present invention relates generally to nerve stimulation, and more particularly to cranial nerve stimulation to stimulate or enhance cardiac capillary growth and cardiac output in heart failure patients.

Heart failure is a cardiac condition or disorder characterized by an abnormal cardiac function—specifically, low cardiac output—that leaves the heart unable to meet the circulatory, oxygen replenishing needs of the body. An estimated 2 million or more individuals in the United States meet the clinical definition of heart failure, making this disorder a major health problem. Although some of the affected individuals are relatively symptom free, those with severe heart failure have very little physical endurance and may be bedridden. Heart rate is one of the major determinants of myocardial oxygen consumption.

It is customary to lower the patient's heart rate as a method of treating heart failure. A lowered heart rate has the effect of improving the oxygen balance in the heart by reducing oxygen demand, while increasing supply through better coronary perfusion, particularly sub-endocardial, during a longer diastolic interval. This scheme is tolerable provided that the working capacity of the individual is not reduced to unacceptably low levels. Because of the complex control system linking heart rate via cardiac output to regulation of blood pressure and peripheral perfusion, most interventions resulting in long term bradycardia involve additional actions on the periphery through direct or indirect neuronal and/or hormonal mechanisms. Physiological bradycardia occurring with exercise training, and pathological bradycardia such as A-V block, are associated with activation of the sympathetic nervous and renin-angiotensin systems and enhanced catecholamine release. One effect of long-term bradycardia common to these situations is myocardial hypertrophy.

With pharmacological methods of inducing bradycardia—for example, by ingestion of beta blockers, calcium channel blockers, or selective bradycardia drugs—it may be difficult to avoid unwanted negative ion inotropy and systemic effects of the drugs, particularly if they are used on a chronic basis. However, even with these side effects, beta blocker therapy is highly beneficial to those patients who can tolerate the side effects. Recently published studies by Carson (*Progress in Cardiovascular Diseases*, Vol 31, No 4, 1999: pp 301–322) reported a 20% reduction in the risk ratio for mortality in patients treated with beta blockers, although patients received little or no improvement in cardiac output.

Brown et al, in an article titled "Long term bradycardia by electrical pacing: a new method for studying heart rate reduction," *Cardiovascular Research* 1994; 28: pp. 1774–1779, demonstrated the benefits of using pacing to lower heart rate in pigs. The researchers used a method of stimulating both the atrial and ventricular chambers of the heart to reduce heart rates from about 130 beats per minute (bpm) to about 85 bpm. The animals were maintained at the lower rate for about six weeks. Autopsies revealed that myocardial capillary was increased by about 20%. No evidence was found of the cardiac hypertrophy associated with pharmacological methods of reducing bradycardia, either on the basis of heart weight or on estimates of myocyte size.

Bilgutay et al., in an article titled "Vagal Tuning," *J Cardiovas. Surg.* 56(1):71–82 described studies in dogs with right vagal stimulation for treatment of supraventricular arrhythmias, angina pectoris, and heart failure. The experiments involved right vagus nerve stimulation and resulted in a selection of amplitude of 6 to 10 volts, a frequency of 10 pulses per second, and 0.2 msec pulse duration. In all experiments, the coronary flow remained constant. However, the heart rate was decreased 35 to 50 percent. The increase in percentage of coronary flow per heart beat was found to be 75 to 100 per cent. In another experiment, Bilgutay administered Isuprel to induce tachycardia, which increased heart rate from 170 bpm to 240 bpm. He then stimulated the vagus nerve and reduced the heart rate from 240 bpm to 120 bpm. The ventricular and aortic pressures were unchanged by vagus stimulation, whereas the systole and diastole were prolonged. These results indicated the contractility of the heart was increased in this model of tachycardia, while the slower rate was maintained, resulting in an increase in cardiac efficiency due to greater stroke output. Although he discussed the potential benefits of treating a failing heart, none of the experiments involved models of heart failure, nor did he anticipate increased capillary growth.

Feliciano et al, in an article titled "Vagal nerve stimulation during muscarinic and beta-adrenergic blockade causes significant artery dilation," *Journal of the Autonomic Nervous System*, 68 (1998), pp. 78–88, demonstrated that vagal nerve stimulation in dogs significantly dilates the coronary arteries and significantly increases coronary artery blood flow. Stimulation was performed at frequencies of 10, 15, 20, and 30 Hertz (Hz). In these studies, the muscarinic and beta-adrenergic receptors were blocked with atropine and propranolol.

Heart rate was controlled at normal rates by pacing. Feliciano did not demonstrate artery dilation in normal conditions, without atropine, propranolol and rate stabilization by pacing, nor did he demonstrate an increase in capillary growth.

Vagus stimulation of the left cardiac branch of the vagus nerve to lower ventricular heart rate in the presence of atrial fibrillation is described by Geddes et. al. in U.S. Pat. No. 5,690,681, and the more recently issued U.S. Pat. No. 5,916,239. As disclosed in the '681 patent, a closed loop, variable frequency vagal stimulation apparatus was used to control ventricular rate during atrial fibrillation. The apparatus included means for stimulating a vagal nerve at a stimulation frequency which was varied automatically in response to sensed conditions, and a controller having an output connected to the stimulating means. The latter included means for automatically and continuously adjusting the vagal stimulation frequency as a function of the difference between actual and desired ventricular excitation rates.

The apparatus of the '681 patent was stated to automatically control ventricular rate by vagal stimulation, to minimize pulse deficit during atrial fibrillation. The arterial pulse rate was detected and the ventricular excitation rate and arterial pulse rate were compared. The vagal stimulation frequency was automatically adjusted as a function of the difference between the ventricular excitation rate and the arterial pulse rate.

A number of patents describe various methods of vagus stimulation for the control of ventricular arrhythmias. U.S. Pat. No. 5,203,326 to Collins discloses a pacemaker which detects a cardiac abnormality—a pathologic high rate—and responds with pacing combined with vagus nerve stimulation, to reduce the heart rate from the tachyrhythmia rate to the normal rate. U.S. Pat. No. 5,330,507 to Schwartz describes stimulation of the right or left vagus nerve in response to a ventricular rate exceeding a predetermined threshold characteristic of tachycardia.

European Pat. No. 688577A1 to Holmstrom describes stimulation of the parasympathetic nervous system in the neck in response to detection of a supraventricular arrhythmia. The vagus nerve is a parasympathetic nerve. U.S. Pat. No. 5,700,282 to Zabara describes a process s for monitoring the heart to detect arrhythmias and simultaneous stimulation of the vagus and cardiac sympathetic nerves to stabilize the heart rhythm. U.S. Pat. No. 5,658,318 to Stroetmann describes detecting a state of imminent cardiac arrhythmia from nerve activity signals and administering antiarrhythmia therapy. U.S. Pat. No. 5,522,854 to Ideker describes detection of the ratio of sympathetic to parasympathetic nerve activity and delivering stimulation to afferent nerves u upon detection of a high-risk arrhythmia. None of these patents describe lowering the hear t rate below the normal physiological rate range in heart failure patients to increase growth of capillaries and increase coronary blood flow.

U.S. Pat. No. 5,913,876 to Taylor describes a method of stimulating the vagus nerve near a patient's heart to momentarily stop the heart in order to perform coronary artery bypass graft surgery.

SUMMARY OF THE INVENTION

The present invention is directed to reducing the heart rate in patients suffering from heart failure—a reduction which may be and preferably is to a rate that is lower than the low end of the normal range of the heart rate of a human subject—to promote and enhance coronary capillary growth and coronary blood flow. This is to be contrasted, for example, with the method and purposes disclosed in the aforementioned '681 patent, which is primarily concerned with reducing a pathologic rapid heart rate—a rapid ventricular rate in the presence of atrial fibrillation—to a rate within the normal range, by using vagal stimulation.

According to the present invention, an implanted nerve stimulation device, or neurostimulator (sometimes referred to herein simply as a "device" or a "stimulator"), is employed and programmed to stimulate the vagus nerve at a first prescribed impulse stimulation frequency to reduce the patient's heart rate, particularly the ventricular rate, toward a heart rate within a desired range. The vagal stimulation frequency is automatically adjusted as a function of the difference between the ventricular excitation rate and the desired ventricular rate. In a typical initial sequence, the implanted device commences to stimulate the vagus nerve at one pulse per second (pps), for example. The stimulation is continued at this frequency for about one minute to allow the ventricular rate to stabilize in the presence of the vagal inputs. Then the vagal stimulation rate is increased, for example to about two pps, and the process continues during another stabilization period. Further change in vagal stimulation frequency is made until the ventricular rate is further reduced and ultimately reaches the desired target range for the rate.

According to an aspect of the invention, the target range is typically set at +/−5% to +/−10% of a prescribed target rate, and the amount (or rate) of the increase in the vagal stimulation frequency is preferably reduced—for example, to 0.5 pps, or proportionally less—as the ventricular rate approaches the target rate range. If the ventricular rate falls below the target rate range, this condition is detected and the vagal stimulation frequency is thereupon automatically reduced or vagal stimulation is entirely inhibited, i.e., ceased, depending upon the extent of the deficit. A damped feedback loop with hysteresis can be used to maintain the frequency of stimulation of the vagus nerve at a level just sufficient to substantially sustain the ventricular rate at the target rate or at least within the target rate range, for example. Alternatively, other types of controllers and control mechanisms may be employed.

As an alternative method, the stimulator may be programmed to reduce the ventricular rate on a periodic basis, by concomitantly and proportionally increasing the vagal stimulation frequency, such as for a period of one hour at the preselected reduced ventricular rate, followed by a period of one hour at the patient's normal resting rate range. This type of alternating reduced heart rate/normal heart rate therapy may be useful for those patients that initially have difficulty tolerating the lowered heart rate. Further, the ON/OFF times (of reduced rate/normal rate) may be selected from a range of minutes to hours or days.

According to another important aspect of the invention, an activity sensor such as an accelerometer may be incorporated within or associated with the stimulator to detect physical activity by the patient—even merely a change in position, or slow walking—to trigger either an inhibition of the vagal stimulation, or an adjustment of the vagal stimulation frequency to produce a higher ventricular target rate. In this way, the patient receives the benefit of a more physiologically appropriate higher heart rate during periods of physical activity or exercise. When the patient ceases the physical activity, that condition is detected by the activity sensor and, in response, the stimulation parameters are returned to a level that will ultimately lower the rate to below the resting heart rate range. For a patient experiencing heart failure, this is the reduced ventricular rate according to the invention.

If permitted by the attending physician, the patient may be given a modicum of control over the therapy to adjust the vagal stimulation rate, and thus the heart rate, according to the state of physical activity of the patient—i.e., whether the patient is in a state of rest or engaging in some form of physical activity, even slight. Toward that end, the stimulator device may be implemented, for example, by incorporating in it instead of or in addition to an activity sensor (e.g., an accelerometer), a reed switch which is operable by an external magnet wielded by the patient. When the patient places the magnet over the implant site of the stimulator, the switch operates, for example, to either inhibit vagal stimulation (for increased heart rate when the patient is about to embark in some physical activity) or to initiate vagal stimulation (for reduced heart rate when the patient is entering a state of rest), according to the specific manner in which the device is implemented to respond to operation of the switch.

A different heart rate target and/or rate range may be programmed in the device for magnet-activation, from the heart rate target or rate range selected for the ongoing or prophylactic operation of the stimulator, or from even the activity sensor-triggered target. Additionally, the programming may be devised to initiate a fall-back rate from the elevated heart rate induced by the initial patient-initiated activation, for a more physiologically appropriate heart rate decline when the patient ceases the activity, upon the next patient initiated activation in an activation sequence.

According to a feature of the invention, the device may also be programmed for different heart rate targets or target ranges during daytime and nighttime hours, or otherwise according to the circadian rhythm of the patient, to recognize the normally lower heart rate during sleep or slumber than the rate experienced when the patient is awake.

Therefore, it is a principal object of the present invention to provide a simple method and device by which the heart rate of a patient suffering from heart failure may be reduced by vagal stimulation to a rate which will sustain life but which is below the low end of the normal heart rate range of the patient. It is a related object of the invention to provide such reduction in heart rate through vagal stimulation, with a view to increase myocardial capillary growth, to enhance coronary blood flow, and to increase cardiac output over a sustained period of time.

Another object of the invention is to selectively lower the heart rate of heart failure patients by vagal stimulation in a gradual manner to a rate within a predetermined target rate range below the low end of the normal rate range, and to maintain the heart rate within that target rate range during periods of rest or substantial inactivity of the patient, to produce an increase in coronary blood flow.

Still another object of the invention is to provide for heart rate reduction in heart failure patients by means of vagal stimulation, with allowance for adjustment of the reduced rate as necessary when the patient is engaged in periods of physical activity by either sensing the activity and inhibiting or changing the vagal stimulation accordingly, or by patient-actuated inhibition.

Still another object of the invention is to limit the heart rate in periods of physical activity to a rate which is both safe and appropriate for the heart failure patient.

BRIEF DESCRIPTION OF THE DRAWINGS

The above and other aims, objectives, aspects, features and attendant advantages of the invention will be further understood from the following detailed description of the best mode presently contemplated for practicing the invention, by reference to a presently preferred embodiment and method, taken in conjunction with the accompanying drawings, in which.

DETAILED DESCRIPTION OF THE PREFERRED METHODS AND EMBODIMENTS

Figure 1:
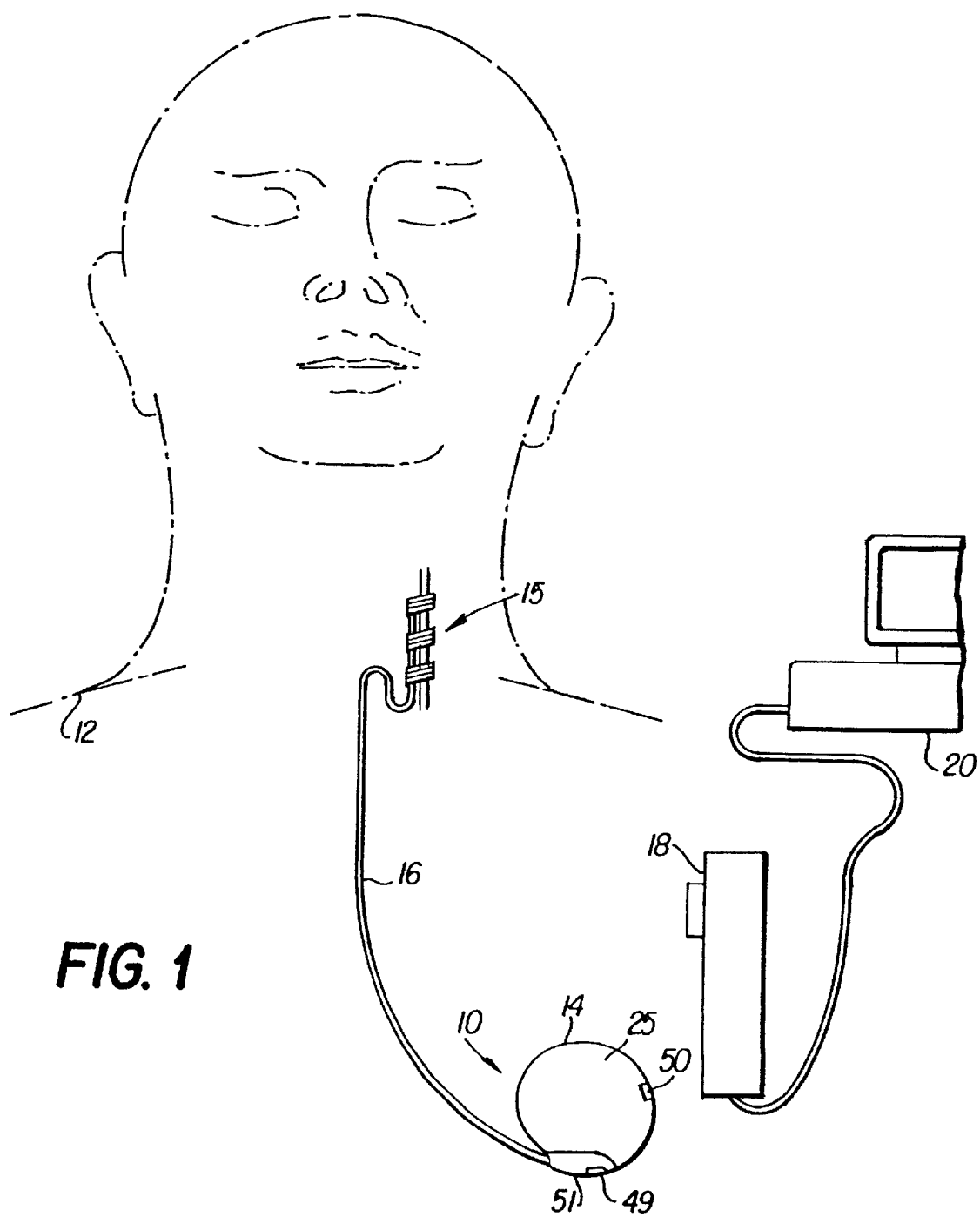
FIG. 1 is a simplified diagram of a neurostimulator device for stimulus generation with associated lead-electrode system implanted in a patient's body, together with related external program console, suitable for practicing the invention.

A simplified version of an implantable neurostimulator device 10 disclosed in U.S. Pat. No. 5,154,172 to R. S. Terry, Jr. et al. (referred to herein as "the '172 patent"), assigned to the assignee of the present application, is illustrated in simplified form in FIGS. 1 and 2, except with respect to certain improvements which are provided in accordance with the present invention as will be described in the course of this discussion.

The stimulus generator 25 of device 10 is generally of thin circular, oval, or rectangular shape and suitably sized for implantation. The device is implanted in a surgically-formed pocket just below the skin, typically but not necessarily in the left pectoral region of a patient 12. The back side of stimulus generator 25 (or the front side, depending on the implanting physician's preference as to the direction in which an electrically conductive insulatively sheathed lead 16 of the neurostimulator device 10 will extend for implantation of electrode array 15 of the lead on the vagus nerve) resides against the pectoral muscle in this example.

The generator housing 14 (typically referred to in the art as a "can" or "case") is composed of biocompatible material, typically a metal such as titanium or medical grade stainless steel, and is hermetically sealed to prevent fluid penetration into the electronic components and battery(ies) (sometimes referred to herein as the "electronics package") contained therein.

A male connector at the proximal end of lead or lead assembly 16 is inserted into a female connector in a header 51 on case 14, to electrically connect the nerve stimulating electrode array 15 at the distal end of lead 16 to the proper node(s) of the electrical circuitry of the electronics package in the stimulus generator. The electrode array is preferably a bipolar stimulating electrode assembly, for example, of the type described in U.S. Pat. No. 4,573,481 to Bullara. The electrical output pulse waveform of stimulus generator 25 is applied through the lead-electrode system to the vagus nerve at a selected location, such as in the cervical location shown in FIG. 1.

The implanted neurostimulator device communicates by telemetry with a programmer and/or monitor (sometimes referred to herein as the "program console") external to the patient's body, by asynchronous serial communication, to selectively control and detect operating states of the device. Conventional external components employed for these purposes may include a programming wand 18 which transmits parameter changes to device 10 and receives device parameter and signal information to be monitored, in conjunction with computer 20 of the program console. Conventional software installed in the computer facilitates physician-controlled adjustment of selected parameters and communication with the implanted device.

Figure 2:
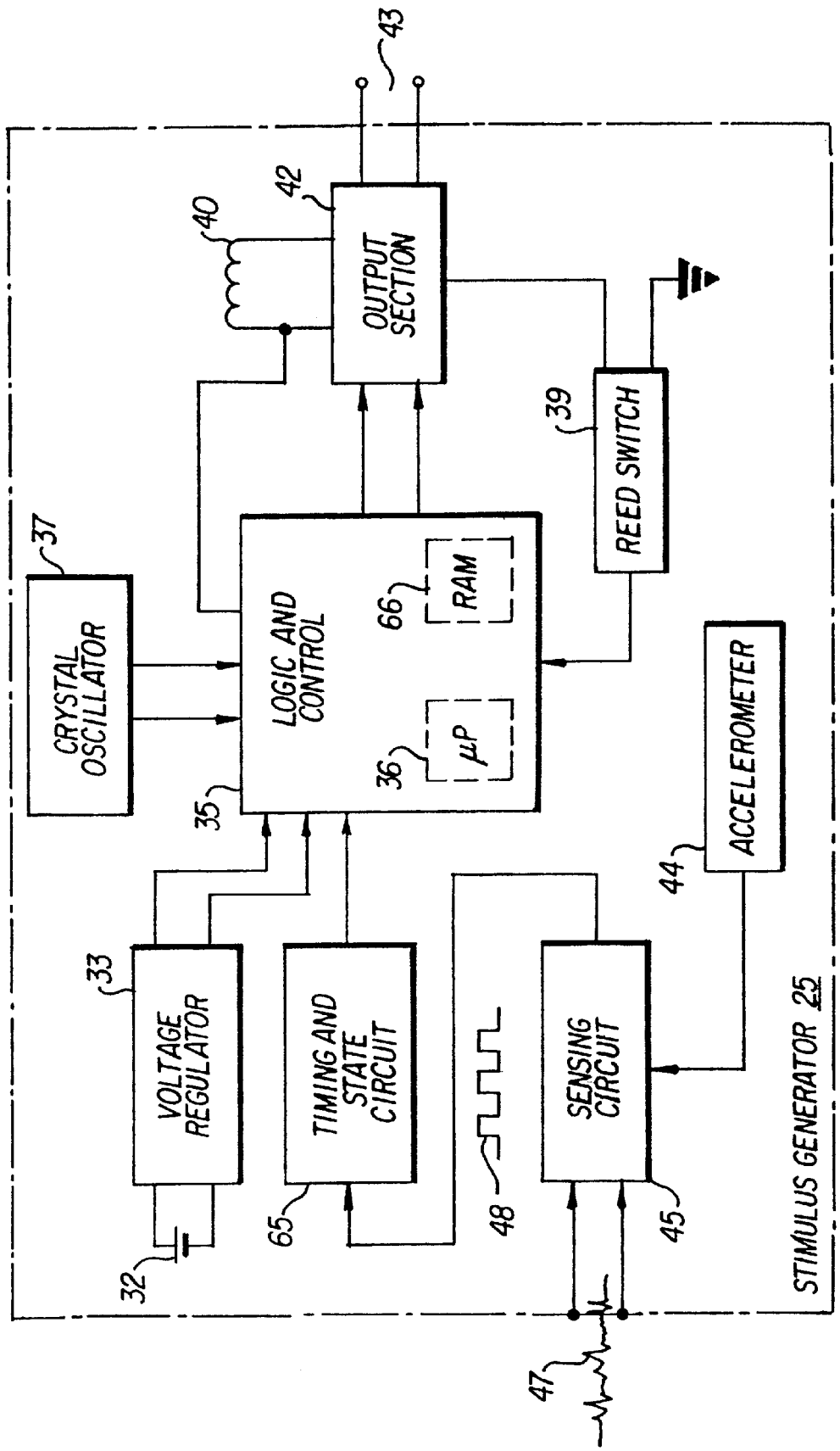
FIG. 2 is a simplified block diagram of an implantable stimulus generator of the type used in the device of FIG. 1, utilizing activity sensing and other detection according to certain preferred methods and embodiments of the present invention

A simplified block diagram of the stimulus generator 25 of implantable device 10 is illustrated in FIG. 2. Generator 25 includes battery(ies) 32, such as a lithium carbon mono fluoride cell, electrically connected to the input of a voltage regulator 33, which powers the device. The regulated output voltage is supplied to a logic and control section 35 and other electronic sections, including a microprocessor 36 that implements and controls the programmable functions of the device. Programmable functions may include the magnitude of current or voltage, the frequency, the pulse width, and the on-time and off-time of output pulses generated by the stimulus generator for application to the lead assembly and thence to the distal electrode array and the nerve on which it is implanted.

The programmability of the device enables the attending physician to selectively tailor its output pulse waveform to modulate the electrical activity of the vagus nerve to provide a prescribed therapy regimen for treatment. Timing of the logic and control and other functions of the stimulus generator is controlled by a precise output frequency signal of a crystal oscillator 37. A magnetically-actuatable reed switch 39 is provided in the event the physician may desire that the patient should be permitted to manually activate the generator for initiating the delivery of its output pulses to the nerve by means of an external magnet (not shown). This may be done for purposes of adjusting the stimulation frequency to increase the heart rate during periods of physical activity by the patient, or to reduce the heart rate toward the lower target range when the activity has ceased for a sufficient interval, as observed in the brief summary of the invention above. The reed switch can also be used to inhibit stimulation in the event the patient experiences discomfort with the programmed therapy or in the event of a perceived malfunction.

Built-in antenna 40 is provided for use in bidirectional telemetry communication between the implanted stimulus generator and the external electronics of the program console, for supplying the programming signals necessary to set or change the output pulse parameters, and to detect device operation, via wand 18 (FIG. 1). Once the generator is programmed, it operates continuously at the programmed settings until they are re-programmed (by the attending physician) by means of the external program console.

Logic/control section 35 controls output circuit 42 for producing the output pulse waveform according to the prescribed therapy. The stimulus generator may be activated continuously or sporadically as necessary for treatment to bring the patient's detected ventricular rate to the target level, or may be controlled at least to some limited extent by the patient's manual activation by use of the external magnet. The programmed output waveform is delivered via the electrical connector in the header of the generator case to lead assembly 16 and stimulating electrode array 15 (FIG. 1). This electrical stimulation produces a predetermined modulation of the electrical activity of the nerve on which the electrodes are implanted, to adjust the ventricular rate of the patient's heart.

Certain techniques of manual and automatic activation of implantable medical devices are disclosed in U.S. Pat. No. 5,304,206 to R. G. Baker, Jr. et al. (referred to herein as "the '206 patent"), which is assigned to the same assignee as the present application. The '206 patent observes that problems may be encountered when a patient seeks to manually activate the device upon sensing a symptom or symptoms of the disorder. According to that patent, means for manually activating or deactivating the stimulus generator include a sensor such as an accelerometer or a piezoelectric element mounted to the inner surface of the generator case and adapted to detect light taps by the patient on the implant site. In this way, the patient is given limited but convenient control over the device operation, to an extent which is determined by the attending physician. Typically, however, in the device and method of the present invention, the patient's ventricular rate is detected and used to automatically adjust the frequency of the vagal stimulation.

For a patient suffering from heart failure, heart rate is reduced to within a rate range below the lower end of the normal resting rate range of the patient. The amount of this reduction is preferably to a rate which is 30 to 45% below the patient's normal heart rate. A conventional implanted rate sensor detects a ventricular rate exceeding the prescribed target rate by application to a comparator that stores the target rate. Certain techniques for implementing the heart rate sensing from the vagus nerve electrode are disclosed in U.S. Pat. No. 5,928,272 to Adkins et al, which is assigned to the same assignee as the present application. This initiates delivery of stimulating electrical pulses to the vagus nerve. The implanted stimulus generator is programmed to stimulate the vagus nerve at an initial pulse stimulation frequency, and, when the patient's heart rate begins to move toward the prescribed target rate, to enter into a specified therapy regimen. For this application, the pulse generator will not be able to sense and stimulate from the same electrode, as is described in the '272' patent. For asynchronous stimulation another sensing electrode is required because if attempts were made to sense off the pacing electrode an event might be missed while a pulse is being delivered. A separate electrode for sensing may be incorporated as an integral part of the pulse generator, for example on the header. Alternatively, a separate lead could be used with the sense tip positioned away from the stimulating electrode. Although not required, the sensing tip could be positioned in, or in close proximity to, the heart. This could also be implemented with one lead body, with a ring sense electrode located around the lead body some distance from the stimulation site. However, if the generator is used exclusively in the synchronous burst mode, a separate sensing electrode would not be required and the nerve stimulation electrode could be used for sensing.

From U.S. Pat. No. 5,916,239 to Geddes, a graph of heart rate versus left vagal stimulation frequency in dogs indicates stimulation at 3.5 Hz limits the rate to about 100 bpm; 6 Hz limits the rate to about 60 bpm; and 10 Hz limits the rate to about 35 bpm. Additional algorithms described in the '239 patent adjust the ventricular rate, particularly while sensing atrial activity.

In an alternate version of the present invention, an amplifier is added to sense the presence of a P wave, indicating atrial contraction. An electrode is inserted in the atrium for increased P wave signal amplitude. Atrial and/or ventricular sensing may be used to control the vagus stimulation rate. Alternatively, a single amplifier-electrode device may be used, which has a signal analyzer to differentiate between the P wave and the R wave.

In this implementation, it is important to stimulate the cardiac branch of the vagus nerve, since stimulation of the main branch of the vagus in the neck below the cardiac branch will not affect the heart rate. The cardiac cervical branch of the vagus nerve provides the most convenient access location for attaching the electrode, as it branches from the main truck of the vagus relatively high in the neck, thus providing a sufficiently long section in the neck for electrode attachment. Stimulation of the left vagus nerve is preferred, although stimulation of the right vagus is an alternative method.

In the preferred regimen, the vagal stimulation frequency is automatically adjusted as a function of the difference between the actual ventricular rate and the target rate. At the commencement of stimulation, the vagus nerve is subjected to stimulation at a frequency of one pulse per second, and this stimulation frequency is sustained for a specified but relatively brief interval of time, e.g., about one minute, to allow the ventricular rate to stabilize at a new level. The vagal stimulation frequency is then increased to a level of about two pulses per second, which is held until the ventricular rate again stabilizes. This regimen continues through the current stabilization period, with further change in vagal stimulation frequency for each measurable reduction in the heart rate and subsequent stabilization interval, until the ventricular rate ultimately reaches the prescribed target rate.

As the ventricular rate approaches the target rate range, the rate of change of increase in the vagal stimulation frequency is preferably programmed, according to the therapy regimen, to decline from one pulse per second between successive stabilization intervals, for example, to 0.5 pulse per second. Alternatively, the controller may take the percentage of difference between the desired and actual ventricular rate, multiplied by a constant factor, and add to the vagus stimulation rate, to achieve the modified vagal stimulation rate. The vagus stimulation frequency is increased to lower the ventricular rate towards to desired range, so long as the atrial-ventricular synchrony is maintained. However, the reduction in ventricular rate is held in a range just above the rate at which atrial-ventricular synchrony is lost. The minimum ventricular rate with which atrial-ventricular rate is maintained can be determined by external monitoring. If the generator has an atrial sense electrode and amplifier, the lower rate can be determined automatically. It has been found that lowering the patient's heart rate to a ventricular bradycardia in a range of from about 30% to 45% of the baseline heart rate, or about 38 bpm to 49 bpm for a rate of 70 bpm, promotes and enhances the growth of coronary blood vessels, and especially the myocardial capillaries, to provide an increase in coronary blood flow through the heart. Cardiac output is expected to be gradually improved over a period of several weeks or longer as a result of increased myocardial capillaries and increased coronary blood flow.

The generator is provided with safeguards to prevent electrical noise from inadvertently lowering the patient's heart rate. First, it should reject any signals above a predefined frequency, such as 5 Hz, as noise. Secondly, a maximum stimulation frequency should be programmed to establish a level which would be physiologically safe for the patient, in the event of noise, so as to prevent the patient's heart rate from being reduced below a safe level. Noise detection algorithms are used, and when noise is detected the vagal nerve stimulation is automatically inhibited.

In an alternative method of providing the stimulation, the stimulation is provided as a burst, which is synchronized with either the P wave or the R wave. The burst typically extends about 150 to 200 msec after the R wave. The advantage of this method is lower stimulator battery usage, due to the lower stimulation duty cycle.

In an alternative therapy protocol of the present invention, the implanted nerve stimulator is programmed to undergo much less frequent changes, so that the ventricular rate of the patient is reduced periodically and held at the reduced level. To that end, the vagal stimulation frequency is proportionally increased, e.g., for a period of, say, one hour at an interim designated ventricular rate. At the conclusion of the one-hour period, followed by a period of one hour in which the vagal stimulation is ceased or adjusted to a lower frequency to allow the heart rate to return to normal resting rates and which will allow an increase in rate up to, but not exceeding, a safe level which will support moderate exercise. Such a protocol or regimen in which the patient's heart rate is alternately reduced and then returned to its normal (for this patient) resting rate, for sufficiently protracted periods which are nominally (but not absolutely necessarily) of the same or substantially similar lengths of time, is desirable in instances where the patient experiences difficulty in tolerating the reduced heart rate.

It is known, for example, that severe bradycardia lowers cardiac output in patients with underlying heart disease, as stroke volume necessarily falls below the maximum the patient experienced prior to the bradycardia. Aerobic exercise capacity also tends to be impaired in heart failure patients, and reducing the heart rate will tend to exacerbate the condition. Exercise, if tolerated, is beneficial, because it promotes increased capillary growth and coronary blood flow, but adds the risk of tachycardia and sudden death at high heart rates.

On the other hand, the regimens practiced according to the invention promote myocardial capillary growth which is desirable in patients with heart failure, and, according to another aspect of the invention, reduction in ventricular rate is intentionally inhibited—at least from the standpoint that the reduction is induced by vagal stimulation attributable to the implanted neurostimulator—during periods in which the patient is detected as undergoing activity. Such detection is enabled by incorporating into the implanted device a conventional activity or exercise sensor, such as an accelerometer 44 (FIG. 2). The output of the accelerometer when indicative of patient activity is used to inhibit or reduce the vagal stimulation to allow assumption of a more physiologically appropriate heart rate, and when indicative of rest is used to increase stimulation toward reduction of the heart rate to the predetermined target rate range.

Even mere changes in position or slow walking are detected by the associated activity sensor to trigger either an inhibition of the vagal stimulation, or an adjustment of the vagal stimulation frequency to allow an intrinsic higher ventricular rate, but which limits the increase in heart rate to a safe level. Consequently, the patient receives the benefit of a more physiologically appropriate higher heart rate at least during the period of physical activity and receives the protection from abnormally high heart rates which could result in tachycardia or sudden death. When the patient returns to a resting condition, the absence of activity (or intrinsic fall-back of the heart rate) is detected by the activity sensor. Vagal stimulation at a frequency to again reduce the ventricular rate below the resting rate is not resumed until patient activity has clearly ceased.

Additionally, in the alternative method described immediately above, the times (i.e., intervals) during which the implanted device is activated for stimulation of the vagus nerve to lower the heart rate and inhibited (or the stimulation is decreased sufficiently) to return the rate back toward the normal resting level may be periodically or even sporadically adjusted as part of the programming of the device, from a range of minutes to hours or even days in length.

Likewise, in each of the therapy regimens practiced according to the invention, the implanted device detects the condition in which the patient's ventricular rate falls below the prescribed target rate, and responds with an automatic reduction of the vagal stimulation frequency or cessation of the stimulation entirely, at least until a recovery to the target rate is detected.

A damped feedback loop with hysteresis can be used to maintain the frequency of stimulation of the vagus nerve at a level sufficient to substantially sustain the ventricular rate within the target rate range. The damped feedback will use the techniques described previously of making small or proportionately small changes in the stimulation rate to increase or decrease the desired heart rate into the desired range. Actually, the damping should be provided on the increasing of the vagal stimulation frequency to reduce the heart rate, whereas no damping is provided on decreasing the vagal stimulation frequency if a decision is made to increase the heart rate because it is too low.

Patient control of the therapy may be permitted to a limited extent by appropriate programming of the implanted device by the attending cardiologist—for example, to allow the patient to adjust the vagal stimulation by temporarily turning it off or adjusting the frequency of stimulation in a limited range, in recognition of the presence or absence of physical activity. This may be done either instead of or in addition to providing an accelerometer in the stimulator. As noted earlier herein, the patient control, if allowed, may be manifested through an external magnet or tapping on the body at or very near the site of the implant, or by any other suitable alternative technique for which the device has been implemented.

According to yet another aspect of the invention, the device is preferably programmed for some patients to undergo vagal stimulation at different target heart rates according to the time of day (e.g., differently during daytime and nighttime hours), or otherwise according to the circadian rhythm of the patient, such as is appropriate to a lower heart rate during sleep or slumber than during the patient's waking hours. This implementation is achieved in part through the incorporation of a conventional clock beyond the clocking provided for operation of the electronics package of the device. The programming for such selected patients may allow a reduction in the target rate during the nighttime hours.

Although certain preferred embodiments and methods of treating heart failure patients according to the invention have been described herein, it will be apparent to those skilled in the field from a consideration of the foregoing disclosure, that variations and modifications of the described embodiments and methods may be made without departing from the true spirit and scope of the invention. For example, although adjusting the frequency of the vagal stimulation is preferred to produce the desired heart rate of the patient suffering from heart failure, the desired rate may be achieved by adjusting the level of some other electrical parameter, such as the magnitude of the vagal stimulation voltage, or of the power applied to achieve the stimulation, or by any other technique which is discernible from the underlying principles of the invention. Accordingly, it is intended that the invention shall be limited only to the extent required by the appended claims and the rules and principles of applicable law.

What is claimed is:

1. A method of treating patients suffering from heart failure, which comprises the steps of:
   stimulating the patient's vagus nerve with electrical pulses generated at a predetermined repetition frequency to reduce the patient's heart rate toward a target rate range below the lowest heart rate of the patient while at rest; and
   keeping the stimulation frequency at a set value when the patient's heart stabilizes at said target rate, to maintain the heart rate within said target rate range.

2. The method of claim 1 including the step of adjusting the stimulation frequency of the pulses while the heart rate is declining, to reduce the rate at which the patient's heart rate approaches said target rate.

3. The method of claim 1, including the step of permitting patient control of the vagal stimulation.

4. The method of claim 3, wherein the step of permitting patient control of the vagal stimulation comprises activating the stimulation.

5. The method of claim 3, wherein the step of permitting patient control of the vagal stimulation comprises inhibiting the stimulation.

6. The method of claim 1 including the step of providing continuous stimulation.

7. The method of claim 1 including the steps of detecting the R wave of the patient's cardiac signal, and providing a burst of stimulation following the detection of the R wave.

8. The method of claim 1 including the steps of detecting the P wave of the patient's cardiac signal, and providing a burst of stimulation following the detection of the P wave.

9. The method of claim 1, including the step of programming the vagal stimulation to alternate between periods of application of said electrical pulses and periods of inhibition thereof.

10. The method of claim 1, including the step of detecting patient activity and, in response to detected activity, inhibiting said vagal stimulation to allow the heart rate to increase above said target rate range.

11. The method of claim 1, including the step of detecting patient activity and, in response to detected activity, adjusting the frequency of said vagal stimulation to allow the heart rate to increase above said target rate range.

12. The method of claim 1 including the step of adjusting the vagal stimulation frequency to limit the maximum heart rate during physical activity.

13. The method of claim 1, including the step of applying said stimulating electrical pulses to the vagus nerve according to the patient's individual circadian cycle.

14. The method of claim 1, including the step of applying said stimulating electrical pulses at different stimulation frequencies according to the time of day.

15. The method of claim 9, wherein said periods of application and said periods of inhibition are substantially the same.

16. The method of claim 9, wherein said periods of application and said periods of inhibition are programmed to be different from one another.

17. A method of treating patients suffering from heart failure to increase cardiac output, which comprises the steps of electrically stimulating the patient's vagus nerve with a sequence of substantially equally spaced pulses, varying the frequency of the stimulating pulses until the patient's heart rate reaches a relatively stable target rate range below the low end of the patient's customary resting heart rate, and then maintaining the frequency of the stimulating pulses at the frequency which ultimately produced the relatively stable target rate range so as not to deviate markedly from said stable target rate at least so long as the patient remains at rest.

18. A device for treating patients suffering from heart failure, to increase cardiac output of the patient, comprising:
   an implantable neurostimulator for applying electrical pulses at a first predetermined frequency to the patient's vagus nerve to lower the patient's heart rate;
   a programmable pulse frequency adjuster for applying the pulses to the vagus nerve at an adjusted frequency which is ultimately sufficient to lower the patient's heart rate to a target rate below the normal heart rate range for a subject at rest; and
   a heart rate detector for maintaining the patient's heart rate at said target rate by controlling said adjuster to continue applying pulses at said adjusted frequency while the patient is nominally at rest.

19. The device of claim 18, further including an implantable activity sensor associated with said neurostimulator for detecting the state of physical activity of the implant patient and for controlling said adjuster to vary the patient's heart rate accordingly.

20. A method of treating patients suffering from heart failure, which comprises the steps of identifying a heart failure patient, and stimulating the vagus nerve to reduce the heart rate of the identified patient to a rate that is lower than the low end of the normal range of the heart rate of a human subject, toward promoting coronary capillary growth and coronary blood flow.

21. The method of claim 20, including the steps of implanting and programming a nerve stimulation device in said identified heart failure patient to stimulate the vagus nerve with a predetermined electrical parameter level to reduce the patient's heart rate toward a heart rate within a desired target range.

22. The method of claim 20, including the steps of implanting and programming a nerve stimulation device in said identified heart failure patient to stimulate the vagus nerve at a first prescribed impulse stimulation frequency to reduce the patient's heart rate toward a heart rate within a desired target range.

23. The method of claim 22, including the step of automatically adjusting the vagal stimulation frequency as a function of the difference between the ventricular excitation rate and the desired ventricular rate.

24. The method of claim 22, including the step of commencing stimulation of the vagus nerve at a relatively low frequency for a period of time sufficient to allow the ventricular rate to stabilize in the presence of the vagal stimulation.

25. The method of claim 24, including the step of increasing the vagal stimulation frequency to a relatively higher frequency than said relatively low frequency for another period of time sufficient to allow the ventricular rate to stabilize in the presence of the vagal stimulation.

26. The method of claim 25, including the step of further changing said vagal stimulation frequency until said ventricular rate is further reduced to ultimately reach a target rate in said desired target range that is lower than the low end of the normal range of the heart rate of a human subject rate.

27. The method of claim 26, including setting said desired target range at +/−5% to +/−10% of said target rate.

28. The method of claim 26, including programming said desired target range.

29. The method of claim 26, including detecting the ventricular rate falling below said desired target range, and thereupon reducing the frequency of said vagal stimulation for return of the ventricular rate to said desired target range.

30. The method of claim 26, including detecting the ventricular rate falling below said desired target range, and thereupon inhibiting said vagal stimulation entirely for return of the ventricular rate to said desired target range.

31. The method of claim 28, including using a damped feedback loop circuit with hysteresis in said nerve stimulation device to maintain the frequency of stimulation of the vagus nerve at a level sufficient to substantially sustain the ventricular rate within said desired target rate range.

32. The method of claim 20, including the steps of implanting and programming a nerve stimulation device in said identified heart failure patient to stimulate the vagus nerve at a prescribed level of an electrical parameter to reduce the patient's heart rate on a periodic basis to a heart rate within a desired target range below the normal resting rate range of said patient, and then to a heart rate within said normal resting rate range.

33. The method of claim 20, including the steps of implanting and programming a nerve stimulation device in said identified heart failure patient to stimulate the vagus nerve at a prescribed level of an electrical parameter to reduce the patient's heart rate on an alternating periodic basis first to a heart rate within a desired target range below the normal resting rate range of said patient, and then to a heart rate within said normal resting rate range.

34. The method of claim 20, including the steps of implanting and programming a nerve stimulation device in said identified heart failure patient to stimulate the vagus nerve at a prescribed level of an electrical parameter to reduce the patient's heart rate to a target heart rate within a desired target range below the normal resting rate range of said patient, including incorporating an activity sensor with said nerve stimulation device to detect physical activity by the patient and thereupon vary said prescribed level to trigger a higher target heart rate.

35. The method of claim 34, including the step of detecting cessation of physical activity by the patient and thereupon returning to said prescribed level to return the heart rate to a rate within said desired target range.

36. The method of claim 35, including the step of programming said device to return to said prescribed level at a fall-back rate which dictates a physiologically appropriate decline of heart rate when said patient ceases said physical activity.

37. The method of claim 21, including the step of providing said device with a patient control means for adjusting said vagal stimulation to vary the heart rate according to the state of physical activity of said patient.

38. The method of claim 21, including the step of programming said device to adjust said vagal stimulation to vary the patient's heart rate according to said patient's circadian rhythm.

39. The method of claim 21, including the step of programming said device to limit the adjustment of vagal stimulation to vary the patient's heart rate to a safe rate below the target rate range.

40. A method of treating patients suffering from heart failure, which comprises the steps of identifying a heart failure patient, and reducing the heart rate of the identified patient to a rate that is lower than the low end of the normal range of the heart rate of a human subject, toward promoting coronary capillary growth and coronary blood flow, including the steps of detecting the patient's heart rate signal, and analyzing the detected heart rate signal for the presence of noise.

41. The method of claim 40, wherein the step of reducing the heart rate is performed by vagal stimulation, and including the step of inhibiting the vagal stimulation when noise is detected.

* * * * *